Feb. 13, 1940. W. I. JOHNSTON Plant Pat. 361
ROSE PLANT
Filed June 9, 1939
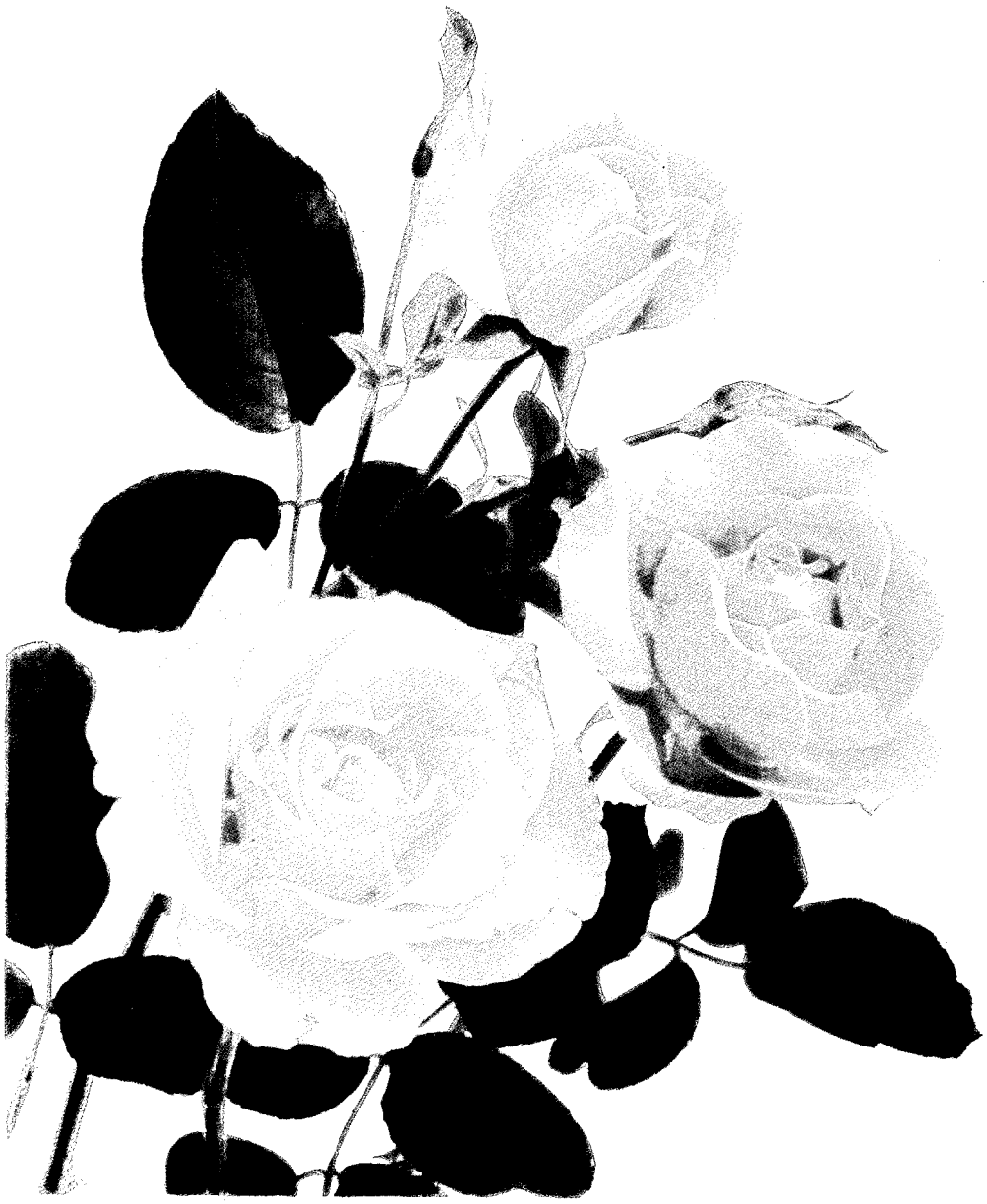
Inventor
W. I. Johnston
By Robb & Robb
Attorneys Patented Feb. 13, 1940

Plant Pat. 361

UNITED STATES PATENT OFFICE

361

ROSE PLANT

Walter Irwin Johnston, Portadown, Ireland, assignor to Jackson & Perkins Company, Newark, N. Y.

Application June 9, 1939, Serial No. 278,369

1 Claim. (Cl. 47—61)

The present invention relates to a new and distinct variety of Hybrid Tea rose plant, the result of a definite effort to produce from two well known McGredy originations having certain very desirable qualities, an improved rose of distinctive coloring, strong fragrance, and vigorous growth.

This new rose was originated by crossing Lesley Dudley with McGredy's Scarlet with the result that novel and attractive color combinations were obtained in the different stages of development of the flower, said combinations running from Spectrum Red when the sepals first divide which fades into Capucine at the base of the petals of the half open flower to Scarlet Red and Rose Doree blending into Capucine Yellow at the lower part of the petals in the fully open flower.

Further a distinction was produced in the petal texture, form of the flower and coloring of foliage.

The new variety has been asexually reproduced and has retained its characteristics.

The following is a detail description of the new variety, all references to color being in accord with Ridgway's Color Standard:

Parentage:
*Seed parent.*—Lesley Dudley.
*Pollen parent.*—McGredy's Scarlet.
Classification:
*Botanic and commercial.*—Hybrid Tea.

*Flower*

Observations made at Newark, New York, in the morning of June 30, 1938.
Blooming habit:
Recurrent—continuous.
Bud:
*Size.*—Small.
*Form.*—Short with flat top. Is not affected by wet or hot weather.
*Color.*—When sepals first divide—Spectrum Red, Plate I. When petals begin to unfurl—Scarlet Red, Plate I. When half blown: inside of petals—between Scarlet Red, Plate I, and Rose Doree, Plate I, fading into Capucine Yellow at base, Plate 3; reverse of petals—between Scarlet Red, Plate I, and Rose Doree, Plate I, fading into Capucine Yellow at base, Plate 3.
*Sepals.*—Serrated, branched "hood" above bud. Curl back when half open.
*Calyx.*—Shape—funnel. Size—Slender. Aspect—smooth.
*Peduncle.*—Length—long. Aspect—rough. Color—Light Cress Green, Plate 31, with overcast of Vandyke Red, Plate 13. Strength—erect, heavy.
*Opening.*—Bud opens well. Is not affected by adverse conditions.
Bloom:
*Size.*—Medium.
*Average size when fully expanded.*—4".
*Borne.*—Several together.
*Stems.*—Medium length, strong.
*Form.*—When first open—cupped. Permanence—outer petals curl back.
*Petalage.*—Double (full but open center). Number of petals under normal conditions—25.
*Color.*—Center of flower—between Scarlet Red, Plate I and Rose Doree, Plate I, showing Capucine Yellow, Plate 3, towards base. Outer petals—between Scarlet Red, Plate I, and Rose Doree, Plate I, showing Capucine Yellow towards base of petal, Plate 3. Base of petals (aiglet)—Empire Yellow, Plate 4. Inside of petals—between Scarlet Red, Plate I, and Rose Doree, Plate I, showing Capucine Yellow towards base of petal, Plate 3. Reverse of petals—between Rose Doree, Plate I, and Peach Red, Plate I, showing Deep Chrome, Plate 3, at base of petal. General tonality from distance—Pink.
*Discolorations.*—General tonality at end of first day—between Scarlet Red and Rose Doree, Plate I. Second day—Scarlet Red to Peach Red, Plate I. Third day—Rose Doree to Peach Red, Plate I.
Petals:
*Texture.*—Thick. Is not affected by wet or hot weather.
*Appearance.*—Inside—satiny. Outside—shiny.
*Form.*—Scalloped.
*Arrangement.*—Irregular. Petaloids in center—few, small.
*Persistence.*—Drop off cleanly.
*Fragrance.*—Strong. Nature—"Old Rose perfume" (Centifolia).
*Lasting quality.*—On the plant and as cut flower—long.
Genital organs:
*Stamens, anthers.*—Medium length, many. Color—Light Cadmium, Plate 4. Arrangement—regular round styles.
*Stamens, filaments (threads).*—Medium length. Color—Pinard Yellow, Plate 4.
*Pollen.*—Light Cadmium, Plate 4.
*Styles.*—Columnar, short, heavy.

*Stigmas.*—Pinard Yellow, Plate 4.
*Ovaries.*—All enclosed in calyx.
Fruit:
Variety is fertile with its own pollen.

*Plant*

Form:
Bush.
Growth:
Very vigorous, branching.
Foliage:
3 to 7 leaflets.
*Size.*—Large.
*Quantity.*—Abundant.
*Color.*—New foliage: upper side—edges Vandyke Red, Plate 13, center Forest Green, Plate 17; under side—Vandyke Red, Plate 13, veins and mid-rib, Light Cress Green, Plate 31. Old foliage: upper side—Varley's Green, Plate 18; under side—Light Elm Green, Plate 17.
*Shape.*—Oval.
*Texture.*—Upper side—leathery. Under side—smooth. Ribs and veins—ordinary.
*Edge.*—Serrated (saw toothed).
*Serration.*—Single, small.
*Rachis.*—Color—Elm Green, Plate 17, on lower side, and Vandyke Red, Plate 13, on upper side. Under side—smooth.
*Stipules.*—Short, bearded.
*Disease resistance.*—Resistant.
Wood:
*New wood.*—Color—Forest Green, Plate 17. Bark—smooth.
*Old wood.*—Color—Dark Cress Green, Plate 31. Bark—smooth.
Thorns (divided in thorns, prickles and short needles):
*Thorns.*—Quantity: on main stalks from base—ordinary; on laterals from stalk—few. Form—narrow base, short, hooked downward. Color when young—Vandyke Red, Plate 13. Position—irregular.
*Prickles.*—Quantity: on main stalks and on laterals—few. Color—Vandyke Red, Plate 13.

I claim:

A new and distinct variety of Hybrid Tea rose plant, characterized particularly by its vigorous growth, the distinct coloring of the flower at the different stages of development thereof, the fragrance and the form of the flower and texture of petals, and the coloring of the foliage, substantially as shown and described.

WALTER IRWIN JOHNSTON.